United States Patent [19]

Swaine et al.

[11] Patent Number: 5,047,331
[45] Date of Patent: Sep. 10, 1991

[54] METHOD AND DEVICE FOR BACTERIAL TESTING

[75] Inventors: Derwent Swaine, Winchester; Eric Y. Bridson, Camberley; Deepak Sawhney, Basingstoke, all of England

[73] Assignee: Oxoid Limited, England

[21] Appl. No.: 110,587

[22] Filed: Oct. 19, 1987

Related U.S. Application Data

[63] Continuation of Ser. No. 574,700, Jan. 27, 1984, abandoned.

[30] Foreign Application Priority Data

Feb. 14, 1983 [GB] United Kingdom ................ 8303096

[51] Int. Cl.⁵ .................... C12Q 1/02; C12Q 1/04; C12M 1/24
[52] U.S. Cl. ........................ 435/29; 435/30; 435/31; 435/32; 435/34; 435/291; 435/292; 435/294; 435/296; 435/807
[58] Field of Search .............. 435/29, 30, 31, 32, 435/34, 291, 292, 294, 296, 807

[56] References Cited

U.S. PATENT DOCUMENTS

| | | | |
|---|---|---|---|
| 2,019,950 | 5/1930 | Bunzell | 435/807 |
| 3,893,892 | 7/1975 | Mehl | 128/764 |
| 3,907,646 | 9/1975 | Wilkins et al. | 435/807 |
| 4,152,213 | 5/1979 | Ahnell | 435/34 |
| 4,170,520 | 10/1979 | Weaver | 435/288 |
| 4,197,369 | 4/1980 | Weaver | 435/807 |
| 4,270,381 | 6/1981 | Demaray | 73/19 |
| 4,314,029 | 2/1982 | Ohtake et al. | 435/807 |

FOREIGN PATENT DOCUMENTS

| | | | |
|---|---|---|---|
| 893844 | 11/1982 | Belgium. | |
| 869845 | 7/1949 | Fed. Rep. of Germany | 128/764 |
| 6704714 | 1/1968 | Netherlands | 604/414 |
| 733893 | 7/1955 | United Kingdom. | |
| 2102947 | 2/1983 | United Kingdom | 435/34 |

OTHER PUBLICATIONS

Stafford et al., Methane Production from Waste Organic Matter, CRC Press Inc., Boca Raton, Fla., (1981), pp. 125-136.

Primary Examiner—Esther L. Kepplinger
Assistant Examiner—Toni R. Scheiner
Attorney, Agent, or Firm—Cushman, Darby & Cushman

[57] ABSTRACT

A method of testing for the growth of bacteria in a sample comprises introducing the sample into a sterile bacterial growth medium in a closed vessel incubating the vessel, and observing a pressure change within the vessel which indicates the growth of bacteria in the sample. A device for doing this comprises a bottle 10 with a pierceable closure 12; and a syringe comprising a cylinder 16 and a piston 18 connected to a hypodermic needle 20 which passes through the closure 12 and preferably extends below the surface of the growth medium in the bottle.

12 Claims, 3 Drawing Sheets

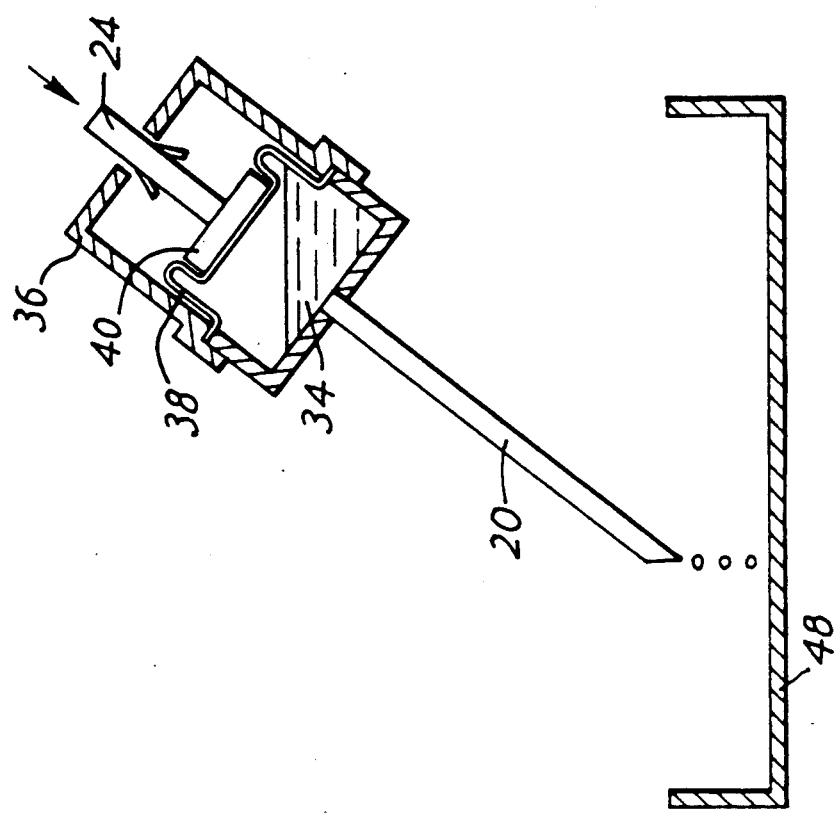
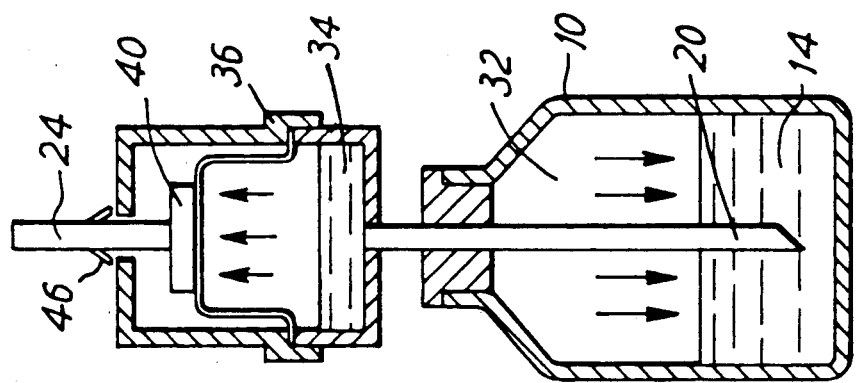
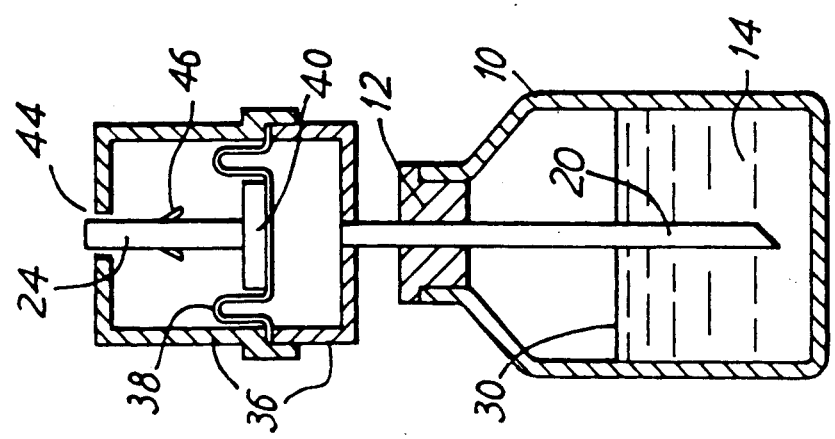

METHOD AND DEVICE FOR BACTERIAL TESTING

This is a continuation of application Ser. No. 574,700, filed Jan. 27, 1984, which was abandoned upon the filing hereof.

In hospital microbiology laboratories, a common technique is to look for the presence of bacteria in a patient's body fluids, particularly blood. Traditionally a bottle of broth (a "blood culture bottle") is set up and a small quantity of blood injected through the enclosing rubber stopper. The bottle is incubated at 37° C., and examined each day for bacterial growth—defined here as slight turbidity in the solution. This can take anywhere from 3-20 days depending on the organism, and as most samples taken eventually turn out to be negative it is a most unrewarding task. Bottles in which growth has taken place are noted as soon as possible, a small quantity of the broth is removed and an identification of the organism made by conventional methods. If it were possible to devise a way of selecting out the positive bottles much faster, a great step forward would have been made.

Attempts have been made to meet this need by mechanising and automating the job of testing for bacterial growth. Equipment is commercially available for doing this by monitoring changes in a variety of physical parameters which occur during bacterial growth. Examples of such parameters are changes in conductivity and impedance. Other systems try to measure metabolic products on a micro scale—one technique measures the amount of $^{14}C$ released from labelled glucose and amino acids. These very small changes need complicated electronic systems for amplification of signals. The equipment required is expensive, and there is general concern that the "black box" approach to microbiology is not necessarily a good thing.

The approach of the present invention is to detect a change in pressure resulting from bacterial growth. This approach requires the formulation of culture media in which bacterial growth does result in a pressure change. In a preferred form, the invention envisages a simple syringe device to give a visual indication of pressure change without the need for any electronic equipment.

In one aspect, the invention thus provides a method of testing for the growth of bacteria in a sample, which method comprises introducing the sample into a sterile bacterial growth medium in a closed vessel, and observing a pressure change within the vessel which indicates the growth of bacteria in the sample.

In another aspect, the invention provides a bacterial testing device comprising a closed vessel containing a sterile bacterial growth medium, means for introducing a sample into the vessel, and means for detecting a pressure change within the vessel.

The method and device have various applications, including a) testing for the presence of bacteria in a sample, as discussed above. The sample may be blood or other body fluids such as urine. Or the sample may be milk or some other beverage. A pressure change will indicate the presence of bacteria in the sample;

b) determining whether an organism is sensitive to an antimicrobial agent. In this case, both the organism and the antimicrobial agent will be introduced into the closed vessel, and a pressure change will indicate that the organism is not sensitive;

c) testing for the presence of an antimicrobial agent in a sample. In this case, a pressure change will indicate the absence of the antimicrobial agent d) identifying a particular organism or a particular antimicrobial agent.

The remainder of this specification is mainly directed to application a).

The nature of the closed vessel is not critical. It may conveniently be a plastics or glass bottle or vial closed with a pierceable autoclavable closure. The size of the vessel should be such that, after introduction of the sample, the headspace is small enough for any pressure change therein (resulting from bacterial growth) to be readily detected.

Incubation may be under aerobic or anaerobic conditions. It will often be necessary to incubate portions of the same sample under both conditions to be sure of detecting bacteria present therein.

If bacterial growth takes place without evolution or absorption of gas, there will be no pressure change and the method and device of this invention will not work. The bacterial growth medium is therefore formulated with the object that bacterial growth be accompanied by pressure change. Preferably bacterial growth is arranged to be by a fermentative, rather than an oxidative, pathway with evolution of gas and consequent pressure increase. While it is probably not possible to formulate a growth medium that satisfies these criteria for all bacteria, it is possible to do so for all commonly encountered pathogenic bacteria. Where necessary, different growth media can be formulated to detect different genera of bacteria suspected to be present in samples.

Using the principles set out below, a growth medium can be formulated to give a pressure increase in the presence of the bacteria that are commonly isolated from blood samples within 24-72 hours of incubation. These bacteria may be aerobic, anaerobic or facultative anaerobes. Such a medium could contain, in addition to the usual basic components (peptides, amino acids, carbohydrates, general growth factors)

a) sodium pyruvate which will be an additional energy source and takes part in catalase reactions to breakdown any superoxide products.

b) menadione and sodium succinate which are essential for growth of Bacteroides spp (important pathogens in anaerobic infections). These are examples of specific metabolites to enable certain organisms to grow quickly; there would be others c) potassium nitrate which will be used by organisms under anaerobic conditions to produce nitrogen and related gases that result in an overall positive pressure change. This is particularly important with Pseudomonas spp which will grow well aerobically but use up the oxygen in headspace resulting in a net negative pressure.

d) gelatin to counter any toxic effects of anticomplementary agents e) sodium thioglycollate and di-thiothreitol to reduce the redox potential $E_h$ of the solution to low levels (providing exacting reducing conditions essential for the growth of obligate anaerobes)

f) sodium bicarbonate which can supply carbon dioxide as a growth stimulant within the medium.

An example of an all purpose formulation is (in grams per liter)—

| | |
|---|---|
| Phosphate buffer | 0.288 |
| Tryptone Soya Broth | 10.0 |
| Gelatin peptone | 10.0 |
| Yeast extract | 5.0 |
| Meat extract | 5.0 |
| Glucose | 1.0 |
| Sodium chloride | 8.0 |
| L-Arginine | 1.0 |
| Sodium Pyruvate | 1.0 |
| Menadione | 0.005 |
| Gelatin | 1.0 |
| Sodium thioglycollate | 0.5 |
| Cysteine HCl | 0.4 |
| Sodium bicarbonate | 0.4 |
| Ammonium chloride | 0.008 |
| Dithiothreitol | 0.2 |
| Adenine sulphate | 0.01 |
| Sodium succinate | 0.01 |
| Potassium nitrate | 2.0 |
| Magnesium sulphate | 0.008 |
| Sodium polyanethol sulphonate | 0.3 |
| pH 7.0 | |

Any kind of pressure-indicating device can in principle be used to detect a pressure increase in the vessel resulting from growth of bacteria. For example, it is possible to measure pressure changes electronically using a pressure transducer connected to a hypodermic needle inserted through the pierceable closure of the bottle.

Alternatively, pressure changes can be detected visually by using a coiled lay-flat tube connected to the hypodermic needle, whereby a pressure increase causes the tube to uncoil.

Another pressure-indicating device is a syringe connected to a hypodermic needle inserted through the pierceable closure of the bottle. A pressure increase causes the piston to rise up the cylinder. When this happens, the volume in the cylinder below the piston may become filled with gas from the bottle. But in a preferred embodiment, the hypodermic needle is caused to extend below the surface of the liquid in the bottle, whereby a pressure increase forces liquid up into the cylinder, thus automatically providing a sample in the syringe which can be removed for analysis. In this case, it is possible to use an indicator which rises by flotation on the top of the liquid in the syringe, instead of a piston sliding in the cylinder.

In the accompanying drawings:

FIGS. 2a, 2b and 2c are sectional side elevations of another such device.

Figure 1:
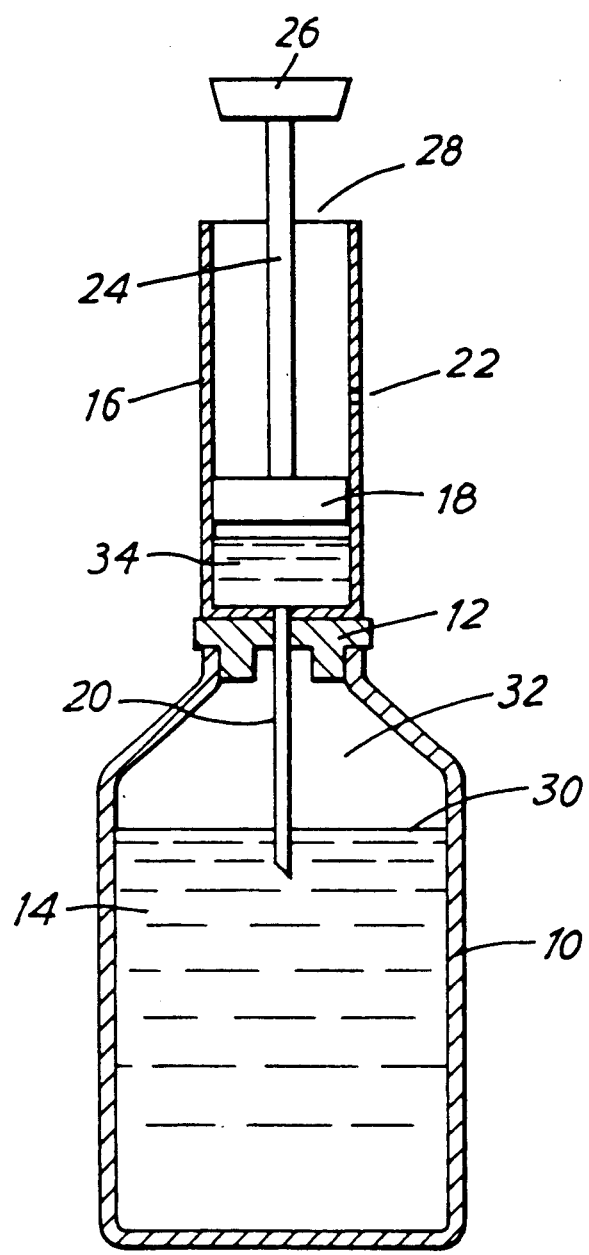
FIG. 1 is a sectional side elevation of a bacterial device according to the invention.

Referring to FIG. 1, a glass bottle 10 is closed with a pierceable autoclavable closure 12 and contains 50 ml of bacterial growth medium 14 into which has been introduced a sample of blood possibly containing bacteria. A hypodermic syringe comprises a cylinder 16, a piston 18 and a hypodermic needle 20. The cylinder has a small vent 22 on one side fitted with a bacterial filter (not shown). The piston carries a shaft 24 on the other end of which is a marker 26 which fits in the open end 28 of the cylinder when the syringe is not in use. The marker is coloured red so as to be easily visible. If desired, a locating device (not shown) may be provided on the closure 12 to ensure that the hypodermic syringe is located centrally on the top of the bottle. The hypodermic needle 20 has been pushed through the closure 12 and inserted into the bottle 10 until its tip is below the surface 30 of the liquid therein. Bacterial growth has taken place in the bottle, resulting in generation of gas in the headspace 32, and this has forced liquid up the needle 20 and into the syringe at 34. This in turn has forced the piston 18 to rise, so that the marker 26 has become visible above the top of the cylinder 16. If more gas is generated in the bottle, the vent 22 will act to prevent the piston from being pushed right out of the cylinder. Venting will also prevent any toxic effects due to a build-up of volatile by-products being produced.

The bottle illustrated is being incubated with a large number of others. During routine inspection, laboratory staff will observe by the marker 26 that bacteria are present in this bottle. The syringe can then be removed and the sample 34 already therein used for analysis.

Although the sample 34 will remain viable in the syringe for up to a week or in some cases longer, it is preferred that bottles should be inspected at least daily, and that samples should be removed for analysis as soon as possible.

The device shown in FIG. 2 is similar to that of FIG. 1, except that the closed container to hold the liquid 34 forced out of the bottle by pressure increase is formed, not by a piston slidable within a cylinder, but by a flexible diaphragm within an open-top vessel. The arrangement of FIG. 2 has the advantage of avoiding possible loss of sterility. Like parts are designated by like numbers in both figures.

Referring to FIG. 2, a glass bottle 10 is closed with a pierceable autoclavable closure 12 and contains 50 ml of bacterial growth medium 14 into which has been introduced a sample of blood possibly containing bacteria. A pressure indicating device comprises a vessel 36, open at its upper and lower ends and divided into two halves by a horizontally extending flexible diaphragm 38. The flexible diaphragm 38 carries a disc 40 supporting a shaft 24 whose upper end is a loose fit in the opening 44 at the top of the vessel 36. The shaft 24 carries a one-way lock 46, which enables the shaft to pass easily upwards through the opening 44, but not to pass accidentally downwards through the opening. The top end of the shaft 24 is coloured red so as to be easily visible. Mounted on the opening at the lower end of the vessel 36 is a hypodermic needle 20.

As shown in FIG. 2a, the hypodermic needle 20 has been pushed through the closure 12 and inserted into the bottle 10 until its tip is below the surface 30 of the liquid therein. The disc 40 is at or near its lowest extremity, and the shaft 24 does not extend significantly above the opening 44.

As shown in FIG. 2b, bacterial growth has taken place in the bottle, resulting in generation of gas in the headspace 32, and this has forced liquid 34 up the needle and into the lower part of the vessel 36. This in turn has flexed the diaphragm 38 causing the disc 40 to rise so that the upper end of the shaft 24 has become visible above the opening 44.

As shown in FIG. 2c, the pressure indicating device has been removed from the bottle, and pressure applied to the upper end of the shaft 24 so as to force liquid 34 down through the hypodermic needle 20 and into a dish 48 for further study. Manual pressure on the shaft 24 overrides the one-way lock 46.

Figure 3:
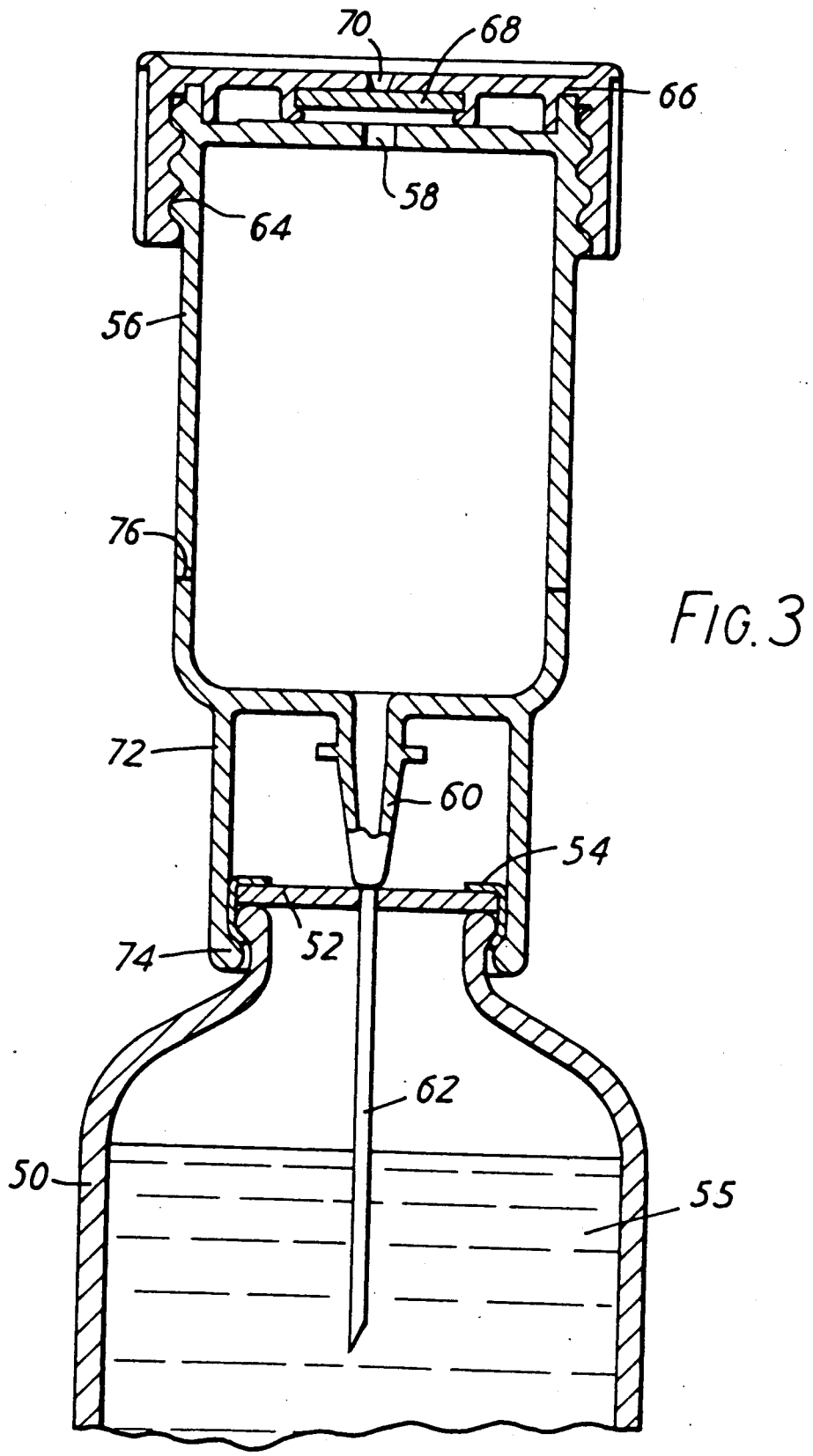
FIG. 3 is a sectional side elevation of yet another such device.

Referring now to FIG. 3, a glass bottle 50 is closed by means of a pierceable autoclavable closure 52 held in place by a clamping ring 54. The bottle has an internal capacity of 59 cc and contains a mixture 55 of 38 ml of culture broth and 5 ml of blood (or other sample to be tested).

The means for detecting pressure change comprise a generally cylindrical vessel 56, closed at its upper end except for a small axial hole 58, and closed at its lower end except for an axial luer connection 60 and hypodermic needle 62. The vessel carries an external thread 64 at its upper end, by means of which a cap 66 has been secured in place. This cap includes a hydrophobic microbial filter 68 which overlies the hole 58, and a small axial vent 70.

At its lower end, the vessel has a cylindrical skirt 72 which terminates at an inwardly facing rib 74. As shown in the drawing, the hypodermic needle 62 has been pushed through the closure 52, and the rib 74 is releasably retained below the clamping ring 54, so that the vessel 56 is held in fixed relationship with the bottle 50. The vessel 56 is of plastics material, clear or translucent above the line 76 and opaque below that line.

The vessel 56 has a capacity of 20 ml. The length of the needle 62 is chosen such that, after about 12–15 ml of liquid has passed up through it from the bottle 50 to the vessel 56, its lower end is clear of the liquid surface in the bottle. Thereafter only gas can pass to the vessel 56. This avoids any danger of overfilling and flooding the vessel.

In use as a blood culture device, the bottle 50 containing the nutrient broth is taken to the patient, and 5 ml of blood introduced. This can be done in one of two ways. Either a sterile air-vent needle is inserted through the closure 52 prior to introduction via another needle of the blood. Or the interior of the bottle is maintained under a controlled reduced pressure so that, when the interior is connected to a syringe containing, say, 20 ml of blood, or indeed when a connection is made direct to the patient's vein, 5 ml of the blood is drawn in thus leaving the interior of the bottle at atmospheric pressure.

The bottle is then taken to the laboratory, where the closure 52 is swabbed with disinfectant and the needle 62 inserted. The device is then incubated, preferably with agitation, at 37° C. The initial expansion resulting from this temperature rise causes a small amount of liquid to pass up through the needle 62 into the vessel 56, but this liquid is masked by the opaque part of the vessel below the line 76. Thereafter, the device is examined periodically. When the liquid surface in the vessel 56 rises above the line 76, indicating the presence of bacteria in the sample, the cap 66 is removed and the liquid sampled through the hole 58 by means of a loop or sterile swab. Microscope examination, direct antibiotic susceptibility tests and subcultures can be made of the sample.

The following Examples illustrate the invention.

EXAMPLE 1

A series of bottles were prepared by providing in each 50 ml of a bacterial growth medium formulated along the lines described above, sealing each with a pierceable closure and then sterilising. Samples containing different bacteria were then introduced into different bottles, and the pressure in each measured by means of a pressure transducer fitted with a hypodermic needle thrust through the closure. The bottles were then incubated for 18 hours, and the pressures measured again. The following results were obtained.

| ORGANISM | INITIAL READING after INOCULATION (arbitrary units) | FINAL READING after 18 hours incubation (arbitrary units) |
| --- | --- | --- |
| Eschericha coli | 3.8 | 6.1 |
| Eschericha coli | 3.8 | 5.8 |
| Pseudomonas cepacia | 3.8 | 4.6 |
| Proteus mirabilis | 3.8 | 5.7 |
| Klebsiella aerogenes | 3.8 | 6.2 |
| Streptococcus pyogenes | 3.8 | 4.6 |
| Streptococcus faecalis | 3.8 | 7.4 |
| Staphlococcus aureus | 3.8 | 6.0 |
| Neisseria gonorrhoeae | 3.8 | 7.5 |
| Neisseria meningitidis | 3.8 | 4.1 |
| Clostridium sporogenes | 3.8 | 10.5 |
| Clostridium tetani | 3.8 | 12.0 |
| Fusobacterium sp | 3.8 | 6.5 |
| Peptostreptococcus sp | 3.8 | 18.5 |
| Bacteriodes fragilis | 3.8 | 8.5 |

EXAMPLE 2

A series of bottles were prepared by providing in each 45 ml of a bacterial growth medium formulated along the lines described above, sealing each with a pierceable closure and then sterilising. 5 ml samples of blood containing known small amounts of different organisms were then introduced into different bottles. Control bottles were also set up to which similar quantities of sterile blood were added. A pressure indicating device as illustrated in FIG. 1 with the bar 18 above the venting hole 22 was inserted into each bottle through the pierceable closure. The bottles were then placed in an incubator and after a period of equilibration (30 minutes) the pressure device was sealed by pushing the bar 18 to the base of the device. The bottles were examined at intervals and the times at which the coloured plungers became visible were noted. The following results were obtained:

| Bottle | Organism under test | Time at which plunger became easily visible. |
| --- | --- | --- |
| A | Control - blood only | Not visible after 5 days. |
| B | Escherichia coli | 18 hours |
| C | Proteus vulgaris | 9 hours |
| D | Staphylococcus oxford | 15 hours |
| E | Pseudomonas aeruginosa | 24 hours |
| F | Bacteroides fragilis | 12 hours |

We claim:
1. A culture test process for culturing a number of samples possibly containing bacteria and identifying any samples among said number which do contain bacteria, by indicating the production of gas during growth of cultures corresponding to said bacteria-containing samples, said process comprising:
 (a) introducing each of said samples possibly containing bacteria into a respective sterile liquid growth medium in a first container of a respective culture test device, the medium being such that it generates gas if bacterial growth occurs;

(b) providing in each said first container a gaseous head space above said liquid medium and a closure for said first container above said head space which is gas tight except for an exit path for liquid via a narrow tube, said tube having a first opening below the surface of said liquid medium in said first container and leading upwards to a respective second, upper liquid container, each said upper liquid container being located above said first container and having a transparent wall for indicating visually the presence of liquid in said upper container, said second, upper liquid container being provided with at least one of a flexible wall for increasing a volume of the interior thereof and means for venting gas from the interior thereof in response to a pressure change in the interior said first container having a gaseous head space above said liquid medium and a closure for said first container which is gas tight except for an exit path via a narrow tube;

said narrow tube opening below the surface of said liquid medium and leading upwards to a second and upper liquid container;

said upper liquid container having a transparent wall for indicating visually the presence of said liquid in said upper liquid container;

said upper liquid container being provided with at least one of a flexible wall for increasing a volume of the interior thereof and means for venting gas from the interior thereof in response to a pressure change in the interior thereof so that liquid can enter said upper liquid container via said narrow tube in response to gas production in said first container with minimal change in interior pressure of said second container;

whereby in use of the device in the event of growth of a bacterial culture in said liquid medium and gas production by said culture, pressure develops in said gaseous head space and drives part of said culture upwards into said upper liquid thereof so that fluid can enter said upper liquid container through said tube in response to gas production in said first container with minimal change in interior pressure of said second container;

(c) incubating said culture test devices together to culture said respective sample in each said device, whereby in the event of bacterial growth and consequent gas production in any of said devices, pressure develops in a corresponding one of said gaseous head spaces and drives part of said respective liquid culture upwards into said respective upper liquid container, thereby to provide visual indication of said gas production in said respective device, thereby to identify the corresponding sample as positive for bacteria.

2. A process according to claim 1, wherein each said first container is a bottle having a pierceable closure and wherein said tube opening below the surface of said liquid medium is a hypodermic needle extending downwards through said closure and dipping into said liquid medium, and wherein pressure change due to gas production by said culture is observed by means of said liquid medium being driven upwards through said needle into said upper liquid container attached to said needle.

3. A process according to claim 1, comprising the additional step of removing each respective upper container and analyzing part of each of said liquid cultures which has been driven into a respective one of said upper liquid containers by said gas production.

4. A process according to claim 1, wherein said liquid medium in said first container comprises peptides, amino acids, carbohydrates and general growth factors, together with at least one further nutrient medium constituent selected from:
 (a) sodium pyruvate as an additional energy source and to take part in catalase reactions to break down any superoxide products;
 (b) menadione and sodium succinate for growth of Bacteroides species;
 (c) potassium nitrate for nitrogen production by anaerobic denitrifying organisms;
 (d) gelatin to counter any toxic effects of anticomplementary agents;
 (e) sodium thioglycollate and dithiothreitol to reduce the redox potential of said liquid culture medium to low redox levels; and
 (f) sodium bicarbonate to supply carbon dioxide.

5. A process as in claim 1, wherein said step of providing includes providing means to mask liquid located in said second container below a predetermined level, thereby to mask any liquid which passes upwards into said second liquid container as a result of temperature rise during incubation.

6. A process according to claim 4, wherein said liquid medium comprises pyruvate, menadione, succinate, nitrate, gelatin, thioglycollate and dithiothreitol, whereby gas production is obtained from aerobic, anaerobic or facultatively anaerobic organisms commonly isolated from blood samples.

7. A culture test device for culturing a sample possibly containing bacteria and identifying whether said sample contains bacteria by providing indication of the production of gas during growth of said bacteria, said device comprising:
 a first container containing a sterile liquid bacterial growth medium which generates gas as bacterial growth occurs; container, thereby to provide visual indication of said gas production in said culture and to identify the sample as positive for bacteria.

8. A test device according to claim 7, wherein said first container is a bottle having a pierceable closure and wherein said tube opening into said liquid medium is a hypodermic needle extending through said closure and dipping below the surface of said liquid medium, whereby pressure change due to gas production by culture of bacteria in use of said device can be observed by means of said liquid medium being driven through said needle into said second liquid container attached to said needle.

9. A test device according to claim 7, wherein said narrow tube opens at predetermined depth below the surface of said liquid medium, whereby in use after a predetermined portion of said liquid medium has been driven upwards through said tube, only gas from the headspace can afterwards pass therethrough.

10. A device as in claim 7, wherein said upper liquid container has means to mask liquid located therein below a predetermined level, thereby to mask any liquid which in use passes upwards into said upper liquid container as a result of temperature rise during incubation.

11. A device as in claim 7, wherein said means for at least one of increasing a volume and venting gas comprise at least one of a vent, a diaphragm, and a flexible wall.

12. A process according to claim 1, wherein each said upper liquid container is provided with a vent covered with a microbial filter.

* * * * *